(12) United States Patent
Wang et al.

(10) Patent No.: US 12,154,193 B2
(45) Date of Patent: *Nov. 26, 2024

(54) IMAGE RECONSTRUCTION METHOD FOR COMPUTED TOMOGRAPHY

(71) Applicant: RENSSELAER POLYTECHNIC INSTITUTE, Troy, NY (US)

(72) Inventors: Ge Wang, Loudonville, NY (US); Wenxiang Cong, Albany, NY (US); Qingsong Yang, Troy, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 13 days.

This patent is subject to a terminal disclaimer.

(21) Appl. No.: 17/859,061

(22) Filed: Jul. 7, 2022

(65) Prior Publication Data

US 2022/0405989 A1     Dec. 22, 2022

Related U.S. Application Data

(63) Continuation of application No. 16/481,298, filed as application No. PCT/US2017/034011 on May 23, 2017, now Pat. No. 11,423,591.

(60) Provisional application No. 62/340,194, filed on May 23, 2016.

(51) Int. Cl.
    *A61B 6/03*          (2006.01)
    *G06T 11/00*       (2006.01)

(52) U.S. Cl.
    CPC ............ *G06T 11/003* (2013.01); *A61B 6/032* (2013.01); *G06T 2211/408* (2013.01)

(58) Field of Classification Search
None
See application file for complete search history.

(56) References Cited

U.S. PATENT DOCUMENTS

| | | | |
|---|---|---|---|
| 6,434,214 B1 | 8/2002 | Kawai et al. | |
| 7,697,658 B2 | 4/2010 | Wang et al. | |
| 8,811,700 B2 | 8/2014 | Wang et al. | |
| 8,862,206 B2 | 10/2014 | Wang et al. | |
| 11,423,591 B2 * | 8/2022 | Wang ................... | G06T 11/003 |
| 2007/0276215 A1 | 11/2007 | Ziegler | |
| 2010/0054394 A1 | 3/2010 | Thibault et al. | |

(Continued)

FOREIGN PATENT DOCUMENTS

| | | |
|---|---|---|
| CN | 103191927 | 7/2013 |
| WO | 2014176328 | 10/2014 |

OTHER PUBLICATIONS

International Search Report and The Written Opinion, International Application No. PCT/US2017/034011 dated Jul. 21, 2017, mailed Jul. 24, 2017.

*Primary Examiner* — Edwin C Gunberg
*Assistant Examiner* — Mamadou Faye
(74) *Attorney, Agent, or Firm* — Barclay Damon LLC; Anthony P. Gangemi

(57) ABSTRACT

Systems and methods for reconstructing images for computed tomography are provided. Image reconstruction can be based on a realistic polychromatic physical model, and can include use of both an analytical algorithm and a single-variable optimization method. The optimization method can be used to solve the non-linear polychromatic X-ray integral model in the projection domain, resulting in an accurate decomposition for sinograms of two physical basis components.

20 Claims, 6 Drawing Sheets

(56) References Cited

U.S. PATENT DOCUMENTS

2011/0105880 A1    5/2011   Yu et al.
2013/0077843 A1    3/2013   Bruder et al.

* cited by examiner

IMAGE RECONSTRUCTION METHOD FOR COMPUTED TOMOGRAPHY

CROSS REFERENCE TO RELATED APPLICATION

This application is a continuation of U.S. Utility patent application Ser. No. 16/481,298, filed Jul. 26, 2019, which is a 35 U.S.C. § 371 U.S. national stage patent application filing of International Patent Application No. PCT/US2017/034011, filed May 23, 2017, which claims the benefit of U.S. Provisional Patent Application Ser. No. 62/340,194, filed May 23, 2016, which are incorporated herein by reference in their entirety, including any figures, tables, and drawings.

BACKGROUND

Computed tomography (CT) can reconstruct a three-dimensional image of an object from a series of projections, providing important diagnosis information. In clinical CT, an X-ray source is polychromatic, and X-ray detectors are currently operated in a current-integrating mode. Existing image reconstruction methods for dual-energy CT are based on an approximate line integral model. Alvarez et al. proposed an image reconstruction method in the projection domain by solving a non-linear integral equation to decompose dual-energy measurements into two independent sinograms, each of which corresponds to a basis component.

Image-domain reconstruction methods first reconstruct images from the low- and high-energy sinograms using filtered back projection (FBP), and then perform image-domain material decomposition. This type of image-domain reconstruction makes substantial approximations in energy spectra, resulting in quantitatively inaccurate results. All of the existing image reconstruction models have drawbacks.

BRIEF SUMMARY

Embodiments of the subject invention provide novel and advantageous systems and methods for reconstructing images for computed tomography (CT) (e.g., dual-energy CT). Image reconstruction can be based on a realistic polychromatic physical model, and can include use of both an analytical algorithm and a single-variable optimization method. The optimization method can be used to solve the non-linear polychromatic X-ray integral model in the projection domain, resulting in an efficient and accurate decomposition for sinograms of two physical basis components.

In an embodiment, a method for reconstructing a CT image of an object being imaged can comprise: receiving CT data from a CT system; and performing an analytical algorithm and a single-variable optimization method on the data to obtain the reconstructed CT image. The analytical algorithm and a single-variable optimization method can include solving two equations (Equations (5) and (6) discussed herein) simultaneously for every detector element of the CT system at each projection view.

In another embodiment, a system for performing a dual-energy CT scan can comprise: an radiation source (e.g., an X-ray source) and a detector for detecting radiation (e.g., X-ray radiation) from the source, the source and detector being configured for dual-energy CT; at least one processor; and a (non-transitory) machine-readable medium (e.g., a (non-transitory) computer-readable medium), in operable communication with the detector and the at least one processor, having machine-executable instructions stored thereon that, when executed by the at least one processor, perform an image reconstruction method as disclosed herein.

In another embodiment, a system for reconstructing CT images (e.g., dual-energy CT images) can comprise: at least one processor; and a (non-transitory) machine-readable medium (e.g., a (non-transitory) computer-readable medium), in operable communication with the at least one processor, having machine-executable instructions stored thereon that, when executed by the at least one processor, perform an image reconstruction method as disclosed herein.

BRIEF DESCRIPTION OF DRAWINGS

FIG. 14A-1 shows a true region of interest (ROI) image for the phantom of FIG. 13A.

FIG. 14A-2 shows a true region of interest (ROI) image for the phantom of FIG. 13B.

FIG. 14A-3 shows a true ROI image for the phantom of FIG. 13C.

FIG. 14B-1 shows a reconstructed version of the image of FIG. 14A-1, reconstructed using a method according to an embodiment of the subject invention.

FIG. 14B-2 shows a reconstructed version of the image of FIG. 14A-2, reconstructed using a method according to an embodiment of the subject invention.

FIG. 14B-3 shows a reconstructed version of the image of FIG. 14A-3, reconstructed using a method according to an embodiment of the subject invention.

DETAILED DESCRIPTION

Figure 1:
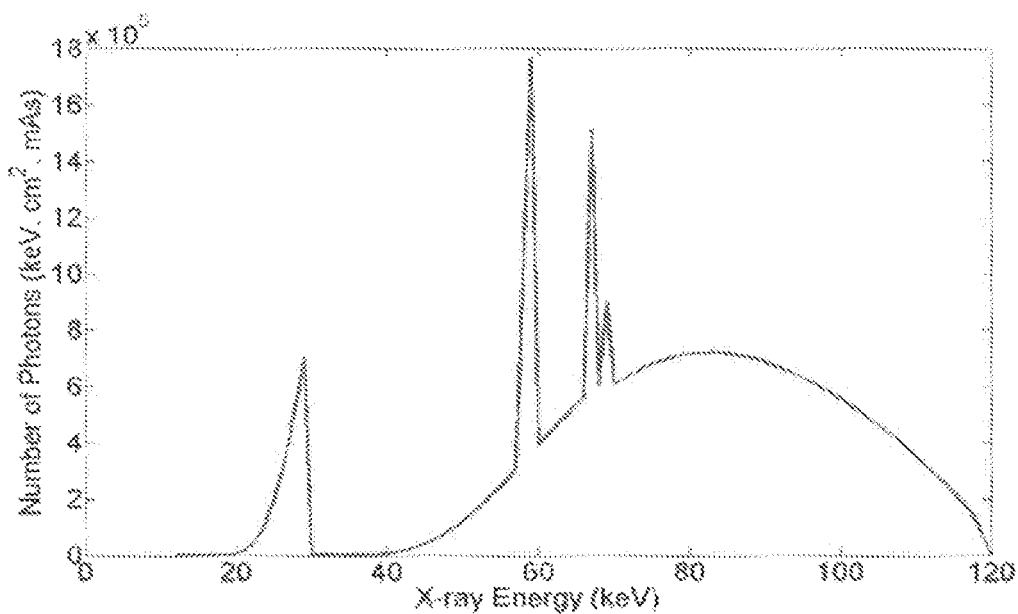
FIG. 1 shows a plot of number of photons (keV-cm$^2$-mAs) versus X-ray Energy (keV) as an energy spectrum generated from an X-ray tube (120 kVp) filtered by tin with a thickness of 0.5 mm.

Embodiments of the subject invention provide novel and advantageous systems and methods for reconstructing images for computed tomography (CT) (e.g., dual-energy CT). Image reconstruction can be based on a realistic polychromatic physical model, and can include use of both an analytical algorithm and a single-variable optimization method. The optimization method can be used to solve the non-linear polychromatic X-ray integral model in the projection domain, resulting in an efficient and accurate decomposition for sinograms of two physical basis components.

In an embodiment, a system for performing a dual-energy CT scan can comprise: an radiation source (e.g., an X-ray source) and a detector for detecting radiation (e.g., X-ray radiation) from the source, the source and detector being configured for dual-energy CT; at least one processor; and a (non-transitory) machine-readable medium (e.g., a (non-transitory) computer-readable medium), in operable communication with the detector and the at least one processor, having machine-executable instructions stored thereon that, when executed by the at least one processor, perform an image reconstruction method as disclosed herein. In another embodiment, a system for reconstructing CT images (e.g., dual-energy CT images) can comprise: at least one processor; and a (non-transitory) machine-readable medium (e.g., a (non-transitory) computer-readable medium), in operable communication with the at least one processor, having machine-executable instructions stored thereon that, when executed by the at least one processor, perform an image reconstruction method as disclosed herein.

In another embodiment, a method for reconstructing a CT image of an object being imaged can comprise: receiving CT data from a CT system; and performing an analytical algorithm and a single-variable optimization method on the data to obtain the reconstructed CT image. The analytical algorithm and a single-variable optimization method can include solving two equations (Equations (5) and (6) discussed herein) simultaneously for every detector element of the CT system at each projection view.

Existing CT image reconstruction methods are based on an approximate line integral model, which ignores X-ray energy information, but lower energy photons are more easily absorbed than higher energy photons, which would cause the X-ray beam to become increasingly harder as it propagates through the object. This physical model mismatch would generate significant beam-hardening artifacts in the reconstructed image. Dual-energy CT is a well-established technique, allowing monochromatic imaging and material decomposition. Current dual-energy X-ray imaging methods include kVp-switching, dual-layer detection, dual-source scanning, and simplistic two-pass scanning. Recent statistical iterative methods incorporate a physical model to reconstruct images directly from dual-energy measurements. These approaches involve a highly nonlinear forward model in the maximum likelihood framework to model the polychromatic measurement, representing a complicated nonlinear optimization problem. Such algorithms can result in great computation cost and slow convergence speed, significantly reducing the practicality of the algorithm. According to algorithms of embodiments of the subject invention, though, the computation cost can be lowered and the convergence speed increased, thereby resulting in a much more practical and efficient image reconstruction method.

Embodiments of the subject invention provide image reconstruction based on a realistic polychromatic physical model, and use both an analytical algorithm and a single-variable optimization method. The optimization method can be used to solve the nonlinear polychromatic X-ray integral model in the projection domain, resulting in an efficient and accurate decomposition for sinograms of two physical basis components. The methodology of such image reconstruction will now be discussed in greater detail.

A CT X-ray source generally emits a polychromatic spectrum of X-ray photons, and the X-ray linear attenuation through the object depends on the object material composition and the photon energy. After a polychromatic X-ray beam passes through the object, the X-ray intensity/measured by a current-integrating detector can be described by the non-linear integral model:

$$I = \int_{E_{min}}^{E_{max}} S(E) \exp(-\int_l \mu(r,E)dr) dE, \qquad (1)$$

where $S(E)$ is the energy distribution (spectrum) of the X-ray source, and $\mu(r, E)$ is the linear attenuation coefficient at an energy $E$ and a spatial position $r$ along an linear path $l$ through the object. During propagation through the object, the X-ray photon population is statistically attenuated according to the nonlinear Equation (1).

It is known that photoelectric absorption and Compton scattering are the two dominant X-ray attenuation processes in the 20 keV-140 keV (keV=kilo-electron Volt) diagnostic energy range. The resulting X-ray linear attenuation coefficient can be represented by:

$$\mu(r, E) = \rho \frac{N_A}{A} (\sigma_{ph} + \sigma_{co}), \qquad (2)$$

where $\rho$, $N_A$, and $A$ are mass density (of a pixel/voxel), Avogadro's number ($6.022 \times 10^{23}$ atom/g-atom) and atomic mass (of a pixel/voxel), respectively. The photoelectric atomic cross section, $\sigma_{ph}$, is formulated as:

$$Z^4 \alpha^4 \frac{8}{3} \pi r_e^2 \sqrt{\frac{32}{\varepsilon^7}} \text{ for } \varepsilon < 1, \qquad (2a)$$

where $\varepsilon = E/511$ keV, $Z$ is the atomic number (of a pixel/voxel), $\alpha$ is the fine-structure constant $1/137$), and $r_e=2.818$ fm (femtometers) is the classical radius of an electron. The Compton atomic cross section, $\sigma_{co}$, is formulated as $Z f_{kn}$, where $f_{kn}$ is the Klein-Nishina function:

$$f_{kn}(\varepsilon) = \qquad (2b)$$
$$2\pi r_e^2 \left( \frac{1+\varepsilon}{\varepsilon^2} \left[ \frac{2(1+\varepsilon)}{1+2\varepsilon} - \frac{1}{\varepsilon} \ln(1+2\varepsilon) \right] + \frac{1}{2\varepsilon} \ln(1+2\varepsilon) - \frac{1+3\varepsilon}{(1+2\varepsilon)^2} \right)$$

With both photoelectric and Compton atomic cross sections, the associated linear attenuation coefficients can be expressed as the product of spatial-dependent and energy-dependent components:

$$\mu(r,s) = a(r)p(\varepsilon) + c(r)q(\varepsilon), \quad (3)$$

where $$a(r) = \rho Z^4/A \quad (3a)$$

is the spatial-dependent photoelectric component, $$c(r) = \rho Z/A \quad (3b)$$

is the spatial-dependent Compton scattering component, $$p(\varepsilon) = N_A \alpha^4 \frac{8}{3} \pi r_e^2 \sqrt{\frac{32}{\varepsilon^7}} \quad (3c)$$

energy-dependent photoelectric component, and $$q(\varepsilon) = N_A f_{kn}(\varepsilon) \quad (3d)$$

is the energy-dependent Compton scattering component.

With dual-energy CT, two distinct spectral measurements are associated with each projection angle. Inserting Equation (3) (and sub-Equations (3a-3d), as applicable) into Equation (1) and using the first X-ray energy spectral measurement, the result is:

$$I_1 = \int_{\varepsilon_{min}}^{\varepsilon_{max}} S_1(\varepsilon) \exp\left(-p(\varepsilon) \int_l a(r)dr - q(\varepsilon) \int_l c(r)dr\right) d\varepsilon \quad (4)$$

$$= \int_{\varepsilon_{min}}^{\varepsilon_{max}} S_1(\varepsilon) \exp\left(-p(\varepsilon) \int_l a(r)dr - q(\varepsilon) \int_l \bar{c}(r)dr\right) \times$$

$$\exp\left(-q(\varepsilon) \int_l [c(r) - \bar{c}(r)]dr\right) d\varepsilon$$

where $\bar{c}(r)$ is an initial estimation of the spatial-dependent Compton scattering component $c(r)$. For example, the mass density, atomic mass, and atomic number of water may be applied for the estimation of $c(r)$. The use of the initial estimation $\bar{c}(r)$ can effectively enhance the accuracy of a low-order Taylor expansion that is applied to the second exponential term in Equation (4). Applying a fourth-order Taylor expansion, the result is:

$$I_1 = \int_{\varepsilon_{min}}^{\varepsilon_{max}} S_1(\varepsilon) \exp\left(-p(\varepsilon) \int_l a(r)dr - q(\varepsilon) \int_l \bar{c}(r)dr\right) \times \left[1 - \right. \quad (5)$$

$$\left. q(\varepsilon)x + \frac{1}{2}q^2(\varepsilon)x^2 - \frac{1}{6}q^3(\varepsilon)x^3 + \frac{1}{24}q^4(\varepsilon)x^4\right]d\varepsilon$$

$$= [p_0(y) + p_1(y)x + p_2(y)x^2 + p_3(y)x^3 + p_4(y)x^4],$$

$$x = \int_l [c(r) - \bar{c}(r)]dr, \quad y = \int_l a(r)dr.$$

Equation (5) is a quartic equation, and there are analytic solutions. The polynomial function with respect to the variable x is strictly convex, typically yielding two real roots and a pair of conjugate complex roots. Generally, the true solution, denoted as x=h(y), can be obtained from the prior range of the x value. Also, applying the second spectral measurement, the projection of the spatial-dependent photoelectric absorption distribution can be computed from the following single variable optimization:

$$y_{min} = \arg\min \|I_2 - \int_{\varepsilon_{min}}^{\varepsilon_{max}} S_2(\varepsilon) \exp[-p(\varepsilon)y - q(\varepsilon)h(y)] d\varepsilon\|. \quad (6)$$

Equation (6) can be effectively solved via single variable optimization; such single variable optimizations options include but are not necessarily limited to golden section search and parabolic interpolation. Therefore, the projections of spatial-dependent photoelectric absorption and Compton scattering images can be effectively determined by solving Equations (5) and (6) simultaneously for every detector element at each projection view. Doing so reconstructs the CT image efficiently and with a high degree of accuracy.

Image reconstruction systems and methods of embodiments of the subject invention can accurately decompose components in the physical basis for dual-energy CT, from which the monochromatic image reconstruction can be obtained. An analytical algorithm and a single-variable optimization method can be combined to solve the nonlinear polychromatic X-ray integral model, resulting in efficient and accurate decomposition for sinograms of two physical basis components, and eliminating or greatly reducing the beam hardening issue associated with related art image reconstruction in CT based on the linear integral model. Image reconstruction can be performed on entire images or on a region of interest (ROI) and/or volume of interest (VOI) of a CT image. Experimental results presented below illustrate the accuracy and advantages of the systems and methods of embodiments of the subject invention, which are advantageous for many fields, including but not necessarily limited to biomedical imaging, nondestructive testing, food inspection, security screening, and industrial evaluation.

Embodiments of the subject invention described herein address the problem of poor and inefficient CT image (e.g., dual-energy CT image) reconstruction by providing a focused technical solution of accurately and efficiently reconstructing CT images (e.g., dual-energy CT images). The embodiments described herein also significantly improve the functioning of machines (e.g., the full CT system) involved in the systems and methods of the subject invention by providing an improved final image when a CT scan (e.g., a dual-energy CT scan) is performed.

The methods and processes described herein can be embodied as code and/or data.

The software code and data described herein can be stored on one or more machine-readable media (e.g., computer-readable media), which may include any device or medium that can store code and/or data for use by a computer system. When a computer system and/or processer reads and executes the code and/or data stored on a computer-readable medium, the computer system and/or processer performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that is capable of storing computer-readable information/data. Computer-readable media should not be construed or interpreted to include any propagating signals. A computer-readable medium of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

A greater understanding of the present invention and of its many advantages may be had from the following examples, given by way of illustration. The following examples are illustrative of some of the methods, applications, embodiments, and variants of the present invention. They are, of course, not to be considered as limiting the invention. Numerous changes and modifications can be made with respect to the invention.

Example 1

A numerical simulation was performed to demonstrate the advantages of the image reconstruction method of embodiments of the subject invention. The X-ray imaging process was simulated with an X-ray tube operated at 120 kVp (kilovolts-peak)/200 mA (milliamps).

Two X-ray energy spectra were generated from the X-ray tube at a single kVp setting by using the Grating Oriented Line-wise Filtration (GOLF) technique, which is also described in detail in International Patent Application No. PCT/US2017/026322, which is hereby incorporated by reference herein in its entirety. GOLF enables interlaced filtration patterns for superior energy separation. An X-ray filtration device can be easily integrated into a CT scanner and its scanning procedure. Depending on the X-ray source type, three main filtration systems/methods can be used, which can be referred to as $GOLF_k$, $GOLF_c$, and $GOLF_s$. $GOLF_k$ can be used for a kVp-switching X-ray source, and can combine an absorption grating and a filter grating disposed between the X-ray source and where a sample/patient to be imaged would be (or is) located (e.g., in front of the X-ray source). GOLFk can synchronize relative motion of the filter and absorption gratings to the kVp switching frequency of the X-ray source. For example, the filter grating can be driven by a high-precision manipulator, such as a piezo-electrical motor for rapid oscillation of one grating relative to the other. Different filter regions can be exposed to X-rays at various time instants, thereby producing low- and high-energy X-rays accordingly. GOLFc and GOLFs can work with a conventional (e.g., non-kVp-switching) X-ray source. GOLFc can use a combination of absorption and filter gratings optimized for an X-ray source without kVp-switching. The X-ray filter grating and/or the X-ray absorption grating can be driven in an oscillation movement relative to each other. GOLFs only requires a filter grating alone that is stationary with respect to the X-ray source. This stationary approach presents a minimum demand for CT hardware enhancement, and in GOLFs, the filter grating can be just a two-strip filter.

As discussed, the GOLF technique is a combination of absorption and filter gratings (placed between the source and patient/object to be imaged) that are driven in relative motion that is synchronized with detector view acquisition. Using micro-technology to fabricate the gratings, the medical CT requirements for a large field of view, large cone angle, and rapid change between filtration settings can be simultaneously met.

Single-slice CT imaging was assumed for the numerical simulation, and a parallel beam geometry was used. The source-to-iso-center distance was set to 54.1 cm, and the source-to-detector distance was set to 94.9 cm. A Shepp-Logan-type phantom was designed to contain 9 sub-regions that were filled with various human tissues. The effective atomic numbers, densities, and atomic masses in these sub-regions, which characterized photoelectric and Compton cross-sections, are listed in Table 1. The phantom diameter was set at 440 mm, and the phantom was placed at iso-center. The phantom was discretized into 512×512 square pixels.

Figure 2:
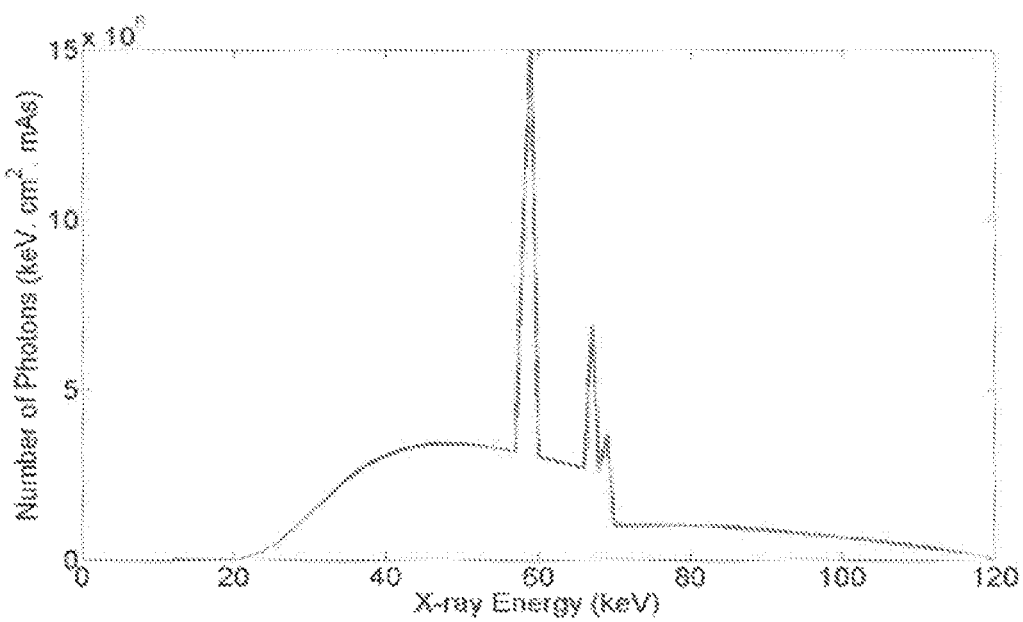
FIG. 2 shows a plot of number of photons (keV-cm$^2$-mAs) versus X-ray Energy (keV) as an energy spectrum generated from an X-ray tube (120 kVp) filtered by tungsten with a thickness of 0.5 mm.

Then, energy-dependent linear attenuation coefficients were synthesized according to Equation (3). The projection datasets were generated for 180 views over a range of 180 based on Equation (1) and using the two energy spectra shown in FIGS. 1 and 2. FIG. 1 shows an energy spectrum generated from an X-ray tube (120 kVp) filtered by tin with a thickness of 0.5 mm, and FIG. 2 shows an energy spectrum generated from an X-ray tube (120 kVp) filtered by tungsten with a thickness of 0.5 mm.

TABLE 1

Parameters of numerical phantom

| Tissue | 1 | 2 | 3 | 4 | 5 | 6 | 7 | 8 | 9 |
|---|---|---|---|---|---|---|---|---|---|
| Z | 3.04 | 4.90 | 4.02 | 5.15 | 5.09 | 4.58 | 5.91 | 5.39 | 5.64 |
| P | 1.00 | 0.96 | 0.99 | 1.07 | 1.06 | 1.03 | 1.20 | 1.06 | 1.10 |
| A | 6.49 | 8.93 | 7.35 | 8.90 | 9.34 | 13.96 | 8.22 | 10.12 | 9.32 |

By interpolation methods, low-energy data and high-energy data were well aligned at each projection view. The projection data were corrupted by Poisson noise to simulate real experiments.

Figure 3:
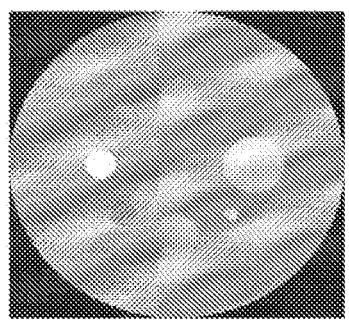
FIG. 3 shows a true Compton scattering phantom image.
Figure 4:
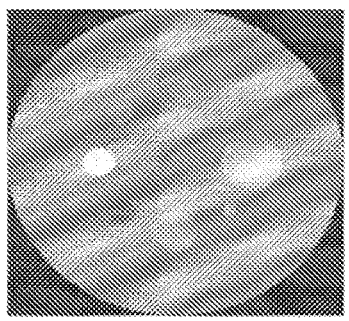
FIG. 4 shows a reconstructed version of the image of FIG. 3, reconstructed using a method according to an embodiment of the subject invention.
Figure 5:
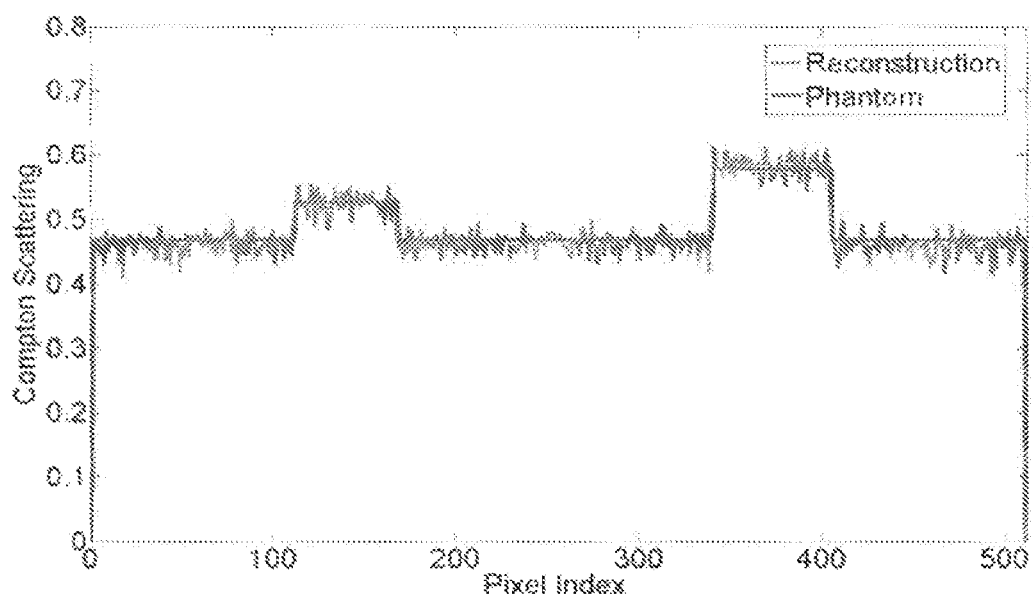
FIG. 5 shows the profiles of the images of FIGS. 3 and 4. The (green) line with the small fluctuations is for the true phantom image (FIG. 3), and the (blue) line with the relatively flat portions and plateau-like sections is for the reconstructed image (FIG. 4).
Figure 6:
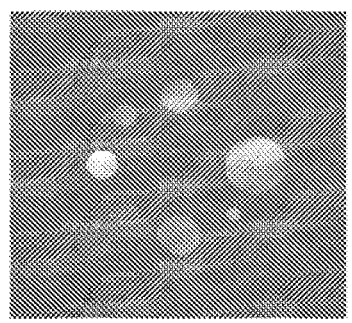
FIG. 6 shows a true photoelectric absorption image of a numerical phantom.
Figure 7:
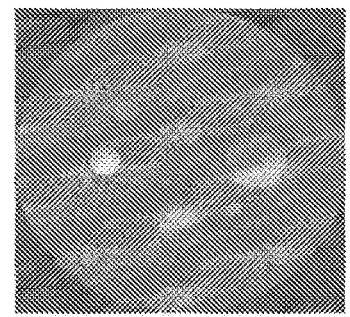
FIG. 7 shows a reconstructed version of the image of FIG. 6, reconstructed using a method according to an embodiment of the subject invention.
Figure 8:
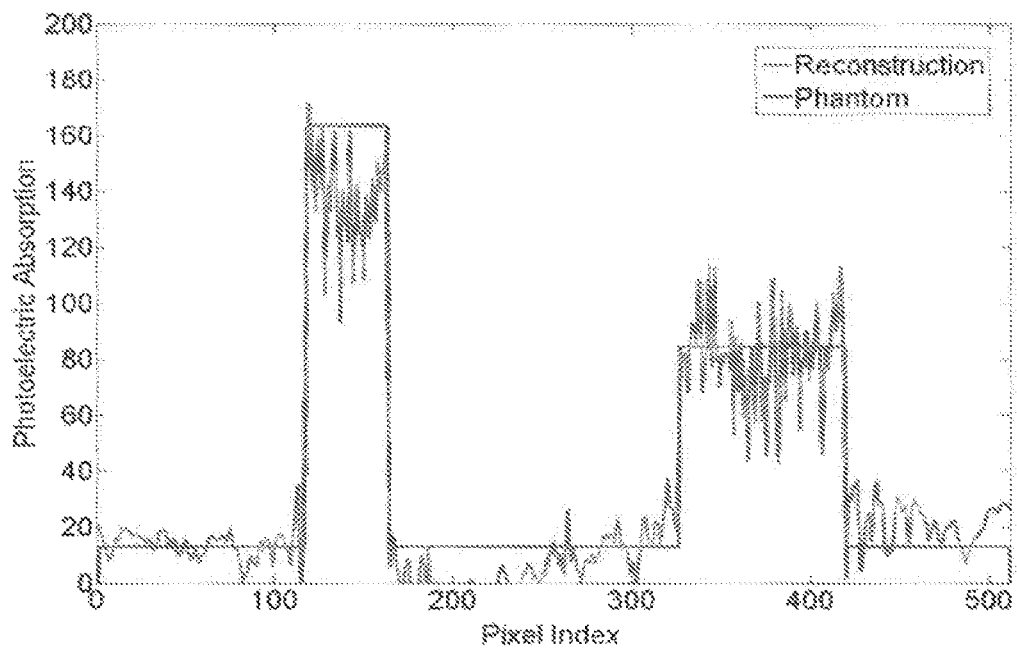
FIG. 8 shows the profiles of the images of FIGS. 6 and 7. The (green) line with the small fluctuations is for the true phantom image (FIG. 6), and the (blue) line with the relatively flat portions and plateau-like sections is for the reconstructed image (FIG. 7).

The algorithm described herein (solving Equations (5) and (6) simultaneously for every detector element at each projection view) was applied for reconstruction of the photoelectric-absorption and Compton-scattering images from the two projection datasets. FIG. 3 shows the true Compton scattering phantom image used, and FIG. 6 shows the true photoelectric absorption image of the numerical phantom used. FIG. 4 shows the reconstructed version of the image of FIG. 3; FIG. 5 shows the profiles of the images of FIGS. 3 and 4 (line with the small fluctuations is for the true phantom image of FIG. 3, and the line with the relatively flat portions and plateau-like sections is for the reconstructed image of FIG. 4); FIG. 7 shows the reconstructed version of the image of FIG. 6; and FIG. 8 shows the profiles of the images of FIGS. 6 and 7 (line with the small fluctuations is for the true phantom image of FIG. 6, and the line with the relatively flat portions and plateau-like sections is for the reconstructed image of FIG. 7).

Referring to FIGS. 3-8, the reconstructed spatial-dependent photoelectric absorption and Compton scattering images are in excellent agreement with the true phantom images, the detailed features are quantitatively accurate, and the beam hardening effect is overcome or at least greatly reduced. Thus, the attenuation coefficient at each energy bin can be computed based on Equation (3) to achieve a monochromatic image reconstruction.

Example 2

For comparison, the numerical simulation of Example 1 was repeated, but the attenuation image reconstruction was performed based on a related art line integral model instead of the advantageous method according to embodiments of the subject invention.

Figure 9:
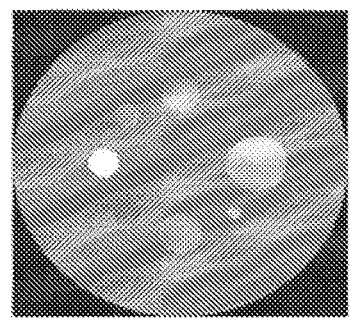
FIG. 9 shows a true photoelectric absorption image of a numerical phantom.
Figure 10:
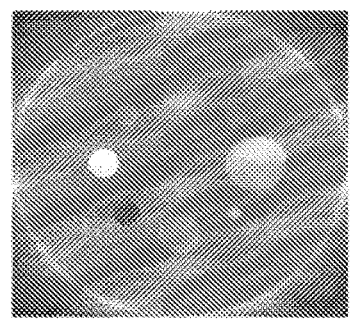
FIG. 10 shows a reconstructed version of the image of FIG. 9, reconstructed using a linear integral model method.
Figure 11:
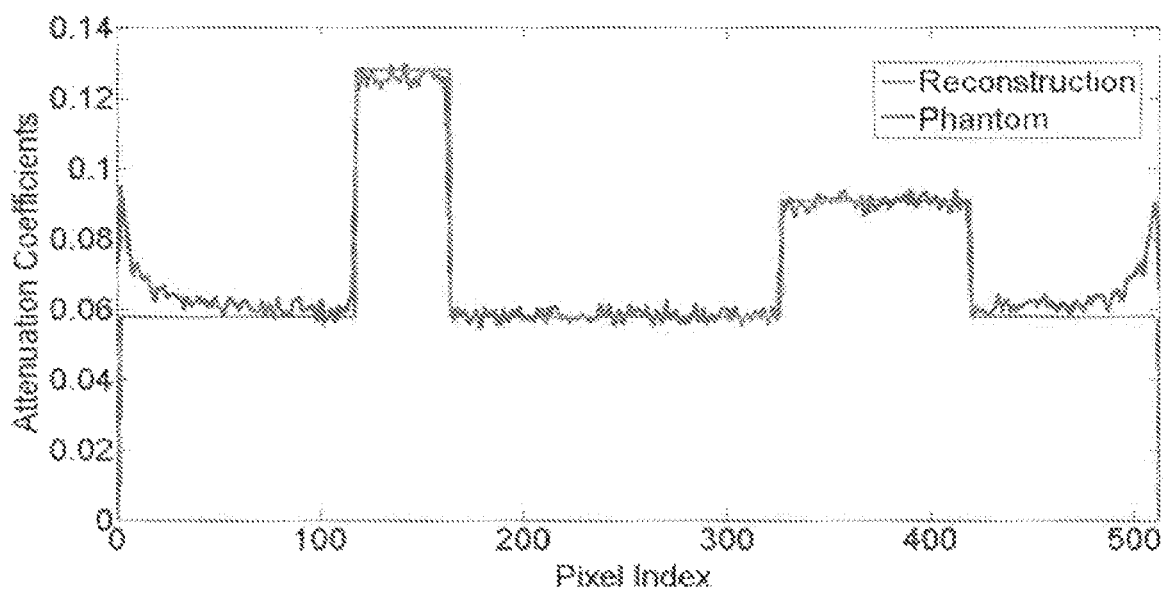
FIG. 11 shows the profiles of the images of FIGS. 9 and 10. The (green) line with the small fluctuations is for the true phantom image (FIG. 9), and the (blue) line with the relatively flat portions and plateau-like sections is for the reconstructed image (FIG. 10).

FIG. 9 shows the true photoelectric absorption image of the numerical phantom used; FIG. 10 shows the reconstructed version of the image of FIG. 9, reconstructed using the related art method; and FIG. 11 shows the profiles of the images of FIGS. 9 and 10 (line with the small fluctuations is for the true phantom image of FIG. 9, and the line with the relatively flat portions and plateau-like sections is for the reconstructed image of FIG. 10). Because of the beam hardening effect, it is observed that the reconstructed image with the line integral model contains cupping artifacts, as plainly seen in FIG. 10.

Example 3

Figure 12:
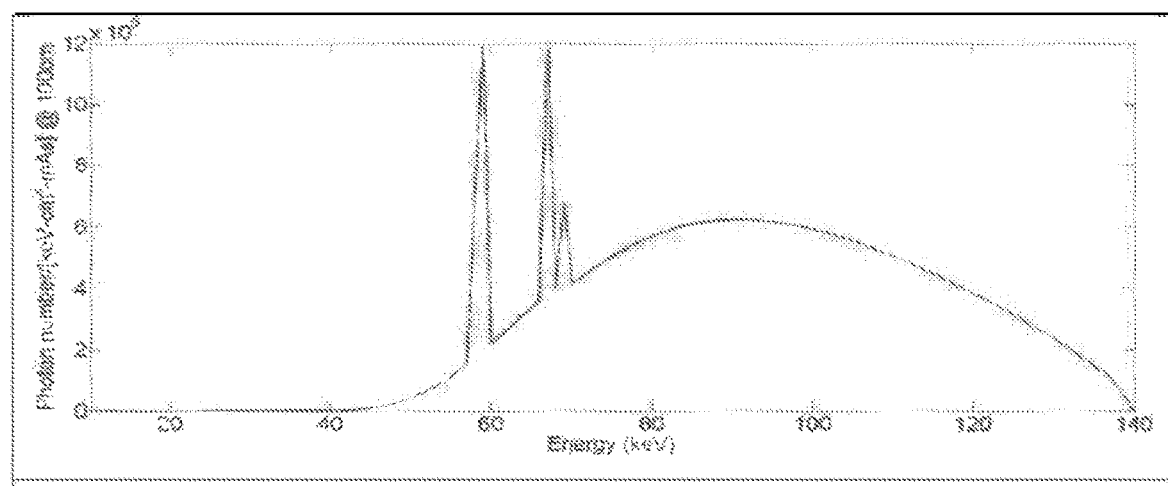
FIG. 12 shows a plot of number of photons (keV-cm$^2$-mAs) versus X-ray Energy (keV) as an energy spectrum generated from an X-ray tube (140 kVp) with aluminum (5 mm-thick) and copper (2 mm-thick) layers to remove low energy photons.
Figures 13A, 13B, 13C:
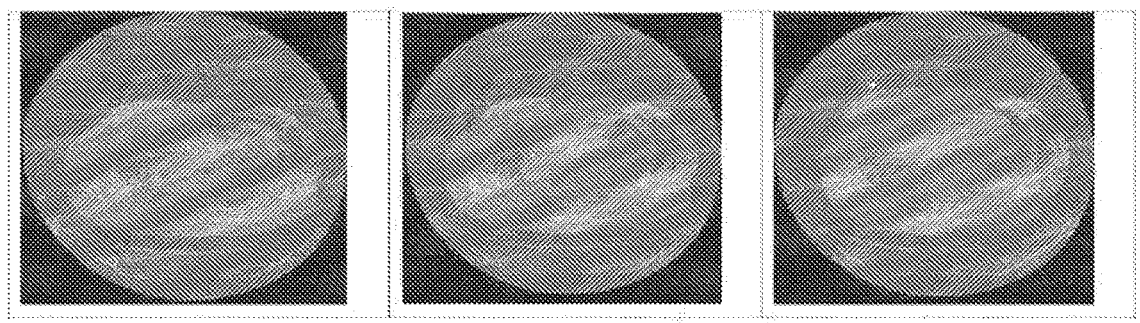
FIG. 13A shows a human chest phantom CT image at a 580th slice.
FIG. 13B shows a human chest phantom CT image at a 600th slice.
FIG. 13C shows a human chest phantom CT image at a 690th slice.
Figures 1, 14A:
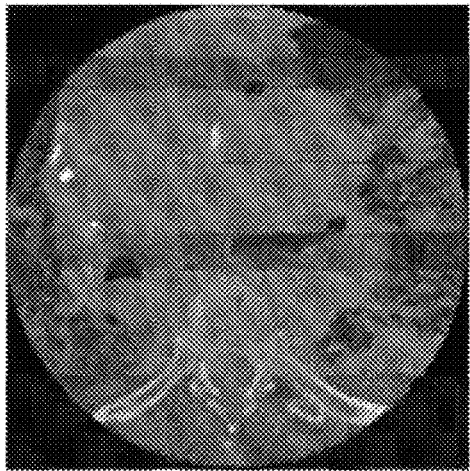
Figures 1, 14B:
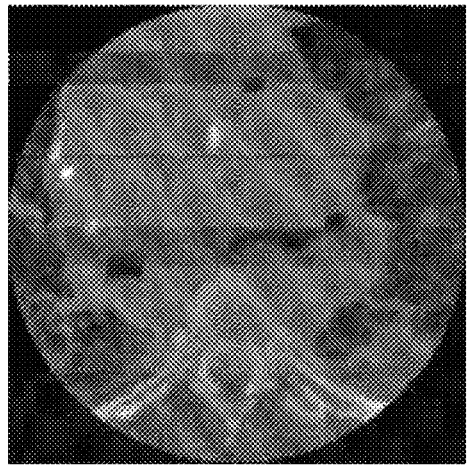
Figures 2, 14A:
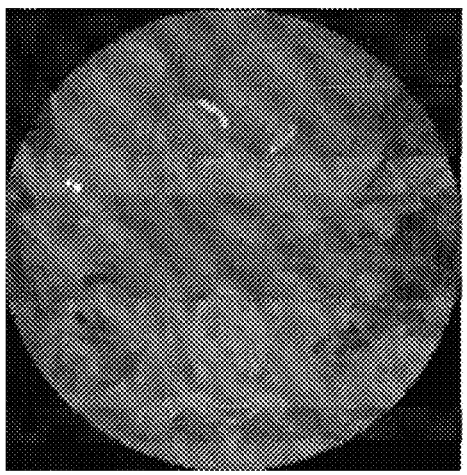
Figures 2, 14B:
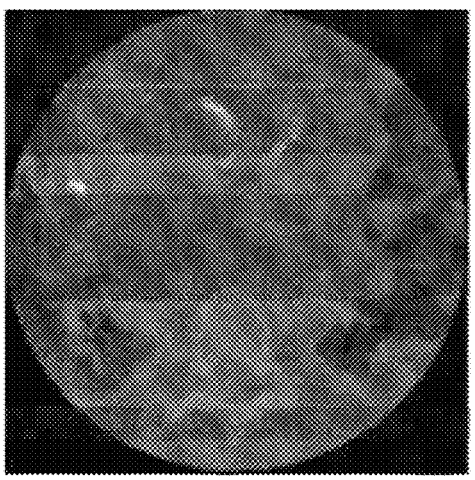
Figures 3, 14A:
Figures 3, 14B:
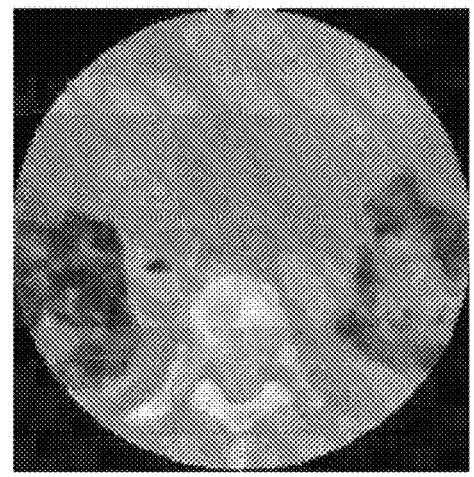

Another numerical simulation was performed to demonstrate the advantages of the image reconstruction method of embodiments of the subject invention. The X-ray imaging process was simulated with an X-ray tube operated at 140 kVp with aluminum (5 mm-thick) and copper (2 mm-thick) layers to remove low energy photons. The polychromatic X-ray spectral profile was estimated using the public software SpekCalc, and is shown in FIG. 12. Representative human chest CT slices were reconstructed in 512×512 pixels, as shown in FIGS. 13A-13C. FIGS. 13A, 13B, and 13C show the human chest phantom CT images at a 580th slice, a 600th slice, and a 690th slice, respectively. The pixel values were converted to linear attenuation coefficients. Then, energy-dependent linear attenuation coefficients were synthesized according to Equation (1). A region of interest (ROI) in the patient chest was selected to contain 256×256 pixels, which is only about 25% of the global area, and the true images of the ROI of FIGS. 13A-13C are shown in FIGS. 14A-1, 14A-2, and 14A-3, respectively. A polychromatic interior scan was focused on the ROI to generate truncated projection data assuming conventional current-integrating detectors that integrate transmitted photons of all energies. The truncated projections were corrupted by Poisson noise. The algorithm described herein (solving Equations (5) and (6) simultaneously for every detector element at each projection view) was applied for reconstruction of the ROI images of FIGS. 14A-1, 14A-2, and 14A-3, and the reconstructed images are shown in FIGS. 14B-1, 14B-2, and 14B-3, respectively. The reconstructed images are in excellent agreement with the true images of the ROI, and the detailed features in the ROI are quantitatively accurate It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein (including those in the "References" section) are incorporated by reference in their entirety, including all figures and tables, to the extent they are not inconsistent with the explicit teachings of this specification.

What is claimed is:

1. A system for performing a dual-energy computed tomography (CT) scan, the system comprising:
a radiation source and a detector for detecting radiation from the radiation source, the radiation source and detector being configured for dual-energy CT;
at least one processor; and
a machine-readable medium, in operable communication with the detector and the at least one processor, having machine-executable instructions stored thereon that, when executed by the at least one processor, perform an analytical algorithm comprising:
simultaneously solving the Equations A and B for every detector element of the CT system at each projection view, wherein Equations A and B are as follows, $$I_1 = \int_{\varepsilon_{min}}^{\varepsilon_{max}} S_1(\varepsilon) \exp\left(-p(\varepsilon)\int_l a(r)dr - q(\varepsilon)\int_l \bar{c}(r)dr\right) \times \left[1 - q(\varepsilon)x + \frac{1}{2}q^2(\varepsilon)x^2 - \frac{1}{6}q^3(\varepsilon)x^3 + \frac{1}{24}q^4(\varepsilon)x^4\right]d\varepsilon \quad (A)$$

$$= [p_0(y) + p_1(y)x + p_2(y)x^2 + p_3(y)x^3 + p_4(y)x^4],$$

$$x = \int_l [c(r) - \bar{c}(r)]dr, \quad y = \int_l a(r)dr$$

and $$y_{min} = \arg\min \left\| I_2 - \int_{\varepsilon_{min}}^{\varepsilon_{max}} S_2(\varepsilon) \exp\left[-p(\varepsilon)y - q(\varepsilon)h(y)\right]d\varepsilon \right\| \quad (B)$$

where S(E) is the energy distribution spectrum of a radiation source of the CT system, r
is a spatial position along a linear path through the object being imaged, $a(r)=pZ^4/A$ is the spatial-dependent photoelectric component of energy detected from the radiation source by a detector configuration of the CT system, $c(r)=pZ/A$ is the spatial-dependent Compton scattering component of the energy detected, $$p(\varepsilon) = N_A \alpha^4 \frac{8}{3}\pi r_e^2 \sqrt{\frac{32}{\varepsilon^7}}$$

is the energy-dependent photoelectric component of the energy detected, $q(\varepsilon)=N_A f_{kn}(\varepsilon)$ is the energy-dependent Compton scattering component of the energy detected, p is the mass density of a pixel/voxel, $N_A$ is Avogadro's number, A is atomic mass of the pixel/voxel, Z is the atomic number of the pixel/voxel, $\varepsilon=E/511$ keV, $\alpha$ is the fine-structure constant ($\approx 1/137$), $r_e=2.818$ femtometers is the classical radius of an electron, h(y) is the true solution of x and $f_{kn}$ is the Klein-Nishina function, $$f_{kn}(\varepsilon) = 2\pi r_e^2 \left(\frac{1+\varepsilon}{\varepsilon^2}\left[\frac{2(1+\varepsilon)}{1+2\varepsilon} - \frac{1}{\varepsilon}\ln(1+2\varepsilon)\right] + \frac{1}{2\varepsilon}\ln(1+2\varepsilon) - \frac{1+3\varepsilon}{(1+2\varepsilon)^2}\right).$$

2. The system according to claim 1, wherein the radiation source of the CT system is an X-ray source such that the radiation energy is X-ray energy.

3. The system according to claim 2, wherein simultaneously solving Equations A and B for every detector element of the CT system at each projection view comprises performing single-variable optimization on Equation B.

4. The system according to claim 3, wherein the single variable optimization is golden section search.

5. The system according to claim 3, wherein the single variable optimization is parabolic interpolation.

6. The system according to claim 3, wherein the single variable optimization is golden section search or parabolic interpolation.

7. The system according to claim 6, wherein simultaneously solving Equations A and B for every detector element of the CT system at each projection view comprises using analytic solutions to solve Equation A.

8. The system according to claim 7, wherein the solution to Equation A yields two real roots and two conjugate complex roots.

9. The system according to claim 8, wherein the true solution of x from Equation A, which is h(y) in Equation B, is obtained from a prior range of x.

10. The system according to claim 9, wherein the radiation source of the CT system is an X-ray source operating in a range of from 20 keV-140 keV.

11. The system according to claim 10, wherein the object to be imaged is a mammalian subject, or a portion thereof.

12. The system according to claim 11, wherein the object to be imaged is a human subject, or a portion thereof.

13. The system according to claim 2, wherein the CT system further comprises at least one grating for filtering at least a portion of the radiation from the X-ray source.

14. A system for reconstructing computed tomography (CT) images, the system comprising:
at least one processor; and
a machine-readable medium, in operable communication with the at least one processor, having machine-executable instructions stored thereon that, when executed by the at least one processor, perform an analytical algorithm comprising:
simultaneously solving the Equations A and B for every detector element of the CT system at each projection view, wherein Equations A and B are as follows, $$I_1 = \int_{\varepsilon_{min}}^{\varepsilon_{max}} S_1(\varepsilon) \exp\left(-p(\varepsilon)\int_l a(r)dr - q(\varepsilon)\int_l \bar{c}(r)dr\right) \times \left[1 - q(\varepsilon)x + \frac{1}{2}q^2(\varepsilon)x^2 - \frac{1}{6}q^3(\varepsilon)x^3 + \frac{1}{24}q^4(\varepsilon)x^4\right]d\varepsilon \quad (A)$$

$$= [p_0(y) + p_1(y)x + p_2(y)x^2 + p_3(y)x^3 + p_4(y)x^4],$$

$$x = \int_l [c(r) - \bar{c}(r)]dr, \quad y = \int_l a(r)dr$$

and $$y_{min} = \arg\min \left\| I_2 - \int_{\varepsilon_{min}}^{\varepsilon_{max}} S_2(\varepsilon) \exp[-p(\varepsilon)y - q(\varepsilon)h(y)]d\varepsilon \right\| \quad (B)$$

where S(E) is the energy distribution spectrum of a radiation source of the CT system, r is a spatial position along a linear path through the object being imaged, $a(r)=\rho Z^4/A$ is the spatial-dependent photoelectric component of energy detected from the radiation source by a detector configuration of the CT system, $c(r)=\rho Z/A$ is the spatial-dependent Compton scattering component of the energy detected, $$p(\varepsilon) = N_A \alpha^4 \frac{8}{3}\pi r_e^2 \sqrt{\frac{32}{\varepsilon^7}}$$

is the energy-dependent photoelectric component of the energy detected, $q(\varepsilon)=N_A f_{kn}(\varepsilon)$ is the energy-dependent Compton scattering component of the energy detected, p is the mass density of a pixel/voxel, $N_A$ is Avogadro's number, A is atomic mass of the pixel/voxel, Z is the atomic number of the pixel/voxel, $\varepsilon=E/511$ keV, $\alpha$ is the fine-structure constant ($\approx 1/137$), $r_e=2.818$ femtometers is the classical radius of an electron, h(y) is the true solution of x and $f_{kn}$ is the Klein-Nishina function, $$f_{kn}(\varepsilon) = 2\pi r_e^2 \left(\frac{1+\varepsilon}{\varepsilon^2}\left[\frac{2(1+\varepsilon)}{1+2\varepsilon} - \frac{1}{\varepsilon}\ln(1+2\varepsilon)\right] + \frac{1}{2\varepsilon}\ln(1+2\varepsilon) - \frac{1+3\varepsilon}{(1+2\varepsilon)^2}\right).$$

15. The system according to claim 14, wherein simultaneously solving Equations A and B for every detector element of the CT system at each projection view comprises performing single-variable optimization on Equation B.

16. The system according to claim 15, wherein the single variable optimization is golden section search or parabolic interpolation.

17. The system according to claim 16, wherein simultaneously solving Equations A and B for every detector element of the CT system at each projection view comprises using analytic solutions to solve Equation A.

18. The system according to claim 17, wherein the solution to Equation A yields two real roots and two conjugate complex roots.

19. The system according to claim 18, wherein the true solution of x from Equation A, which is h(y) in Equation B, is obtained from a prior range of x.

20. The system according to claim 14, wherein the system is configured to reconstruct dual-energy CT images.

* * * * *